(12) United States Patent
Seguin et al.

(10) Patent No.: US 9,005,274 B2
(45) Date of Patent: Apr. 14, 2015

(54) METHOD FOR TREATING A BODY LUMEN (75) Inventors: Jacques Seguin, Windsor (GB);
Gonzague Issenmann, Clichy (FR)

(73) Assignee: Stentys SAS, Paris (FR)

( * ) Notice: Subject to any disclaimer, the term of this patent is extended or adjusted under 35 U.S.C. 154(b) by 1446 days.

(21) Appl. No.: 12/247,077

(22) Filed: Oct. 7, 2008

(65) Prior Publication Data
US 2010/0030324 A1 Feb. 4, 2010

Related U.S. Application Data (60) Provisional application No. 61/086,048, filed on Aug. 4, 2008.

(51) Int. Cl.
*A61F 2/06* (2013.01)
*A61F 2/91* (2013.01)
*A61F 2/856* (2013.01)

(52) U.S. Cl.
CPC . *A61F 2/91* (2013.01); *A61F 2/856* (2013.01); *A61F 2002/067* (2013.01); *A61F 2250/006* (2013.01); *A61F 2230/0054* (2013.01)

(58) Field of Classification Search
CPC ....................................................... A61F 2/06
USPC ........... 623/1.15, 1.11, 1.44, 1.46, 1.42, 1.43; 604/22; 606/194; 424/423
See application file for complete search history.

(56) References Cited

U.S. PATENT DOCUMENTS

| | | |
|---|---|---|
| 4,665,906 A | 5/1987 | Jervis |
| 4,795,458 A | 1/1989 | Regan |
| 4,820,298 A | 4/1989 | Leveen et al. |
| 5,061,275 A | 10/1991 | Wallsten et al. |
| 5,067,957 A | 11/1991 | Jervis |
| 5,514,154 A | 5/1996 | Lau et al. |
| 5,540,713 A | 7/1996 | Schnepp-Pesch et al. |
| 5,545,210 A | 8/1996 | Hess et al. |
| 5,562,641 A | 10/1996 | Flomenblit et al. |
| 5,591,226 A | 1/1997 | Trerotola et al. |
| 5,597,378 A | 1/1997 | Jervis |
| 5,749,825 A | 5/1998 | Fischell et al. |
| 5,766,237 A | 6/1998 | Cragg |

(Continued)

FOREIGN PATENT DOCUMENTS

| | | |
|---|---|---|
| AU | 200151922 A1 | 8/2001 |
| CA | 2 281 775 A1 | 6/2000 |

(Continued)

OTHER PUBLICATIONS

Furui, Shigeru M.D., et al., "Hepatic Inferior Vena Cava Obstruction: Treatment for Two Types with Gianturco Expandable Metallic Stents", Interventional Radiology, 1990, 176:665-670.

(Continued)

*Primary Examiner* — Thomas J Sweet
*Assistant Examiner* — Matthew Schall
(74) *Attorney, Agent, or Firm* — Oliff PLC (57) ABSTRACT

A method for treating a body conduit/lumen having an undesired reduced diameter includes determining a target diameter of the conduit/lumen in a target location of the conduit/lumen, and delivering a self-expanding metal stent in a contracted configuration to the target location. In a fully expanded configuration, the stent has a diameter that is more than 50% larger than the target diameter over an entire length of the self-expanding stent.

29 Claims, 6 Drawing Sheets

(56) References Cited

U.S. PATENT DOCUMENTS

| | | | |
|---|---|---|---|
| 5,769,817 A | 6/1998 | Burgmeier | |
| 5,827,321 A | 10/1998 | Roubin et al. | |
| 5,876,434 A | 3/1999 | Flomenblit et al. | |
| 5,888,201 A | 3/1999 | Stinson et al. | |
| 5,891,108 A | 4/1999 | Leone et al. | |
| 5,911,754 A | 6/1999 | Kanesaka et al. | |
| 5,928,217 A | 7/1999 | Mikus et al. | |
| 5,964,770 A | 10/1999 | Flomenblit et al. | |
| 6,017,362 A | 1/2000 | Lau | |
| 6,066,167 A | 5/2000 | Lau et al. | |
| 6,068,655 A | 5/2000 | Seguin et al. | |
| 6,077,298 A | 6/2000 | Tu et al. | |
| 6,093,203 A | 7/2000 | Uflacker | |
| 6,129,755 A | 10/2000 | Mathis et al. | |
| 6,139,536 A | 10/2000 | Mikus et al. | |
| 6,187,034 B1 | 2/2001 | Frantzen | |
| 6,258,117 B1 | 7/2001 | Camrud et al. | |
| 6,306,141 B1 | 10/2001 | Jervis | |
| 6,312,455 B2 | 11/2001 | Duerig et al. | |
| 6,342,067 B1 | 1/2002 | Mathis et al. | |
| 6,348,065 B1 | 2/2002 | Brown et al. | |
| 6,379,369 B1 | 4/2002 | Abrams et al. | |
| 6,409,754 B1 | 6/2002 | Smith et al. | |
| 6,416,544 B2 | 7/2002 | Sugita et al. | |
| 6,464,720 B2 | 10/2002 | Boatman et al. | |
| 6,478,816 B1 | 11/2002 | Kveen et al. | |
| 6,485,510 B1 | 11/2002 | Camrud et al. | |
| 6,485,511 B2 | 11/2002 | Lau et al. | |
| 6,533,807 B2 | 3/2003 | Wolinsky et al. | |
| 6,540,849 B2 | 4/2003 | DiCarlo et al. | |
| 6,562,067 B2 | 5/2003 | Mathis | |
| 6,568,432 B2 | 5/2003 | Matsutani et al. | |
| 6,572,646 B1 | 6/2003 | Boylan et al. | |
| 6,596,022 B2 | 7/2003 | Lau et al. | |
| 6,602,272 B2 | 8/2003 | Boylan et al. | |
| 6,602,281 B1 | 8/2003 | Klein | |
| 6,602,282 B1 | 8/2003 | Yan | |
| 6,626,937 B1 | 9/2003 | Cox | |
| 6,652,579 B1 | 11/2003 | Cox et al. | |
| 6,666,882 B1 | 12/2003 | Bose et al. | |
| 6,666,883 B1 | 12/2003 | Seguin et al. | |
| 6,679,910 B1 | 1/2004 | Granada | |
| 6,699,280 B2 | 3/2004 | Camrud et al. | |
| 6,706,061 B1 | 3/2004 | Fischell et al. | |
| 6,881,223 B2 | 4/2005 | Penn et al. | |
| 6,887,264 B2 | 5/2005 | Penn et al. | |
| 6,908,479 B2 | 6/2005 | Lau et al. | |
| 6,916,336 B2 | 7/2005 | Patel et al. | |
| 6,929,659 B2 | 8/2005 | Pinchuk | |
| 6,949,120 B2 | 9/2005 | Kveen et al. | |
| 7,029,492 B1 | 4/2006 | Mitsudou et al. | |
| 7,128,758 B2 | 10/2006 | Cox | |
| 2001/0037146 A1 | 11/2001 | Lau et al. | |
| 2001/0037147 A1 | 11/2001 | Lau et al. | |
| 2001/0041930 A1 | 11/2001 | Globerman et al. | |
| 2001/0044648 A1 | 11/2001 | Wolinsky et al. | |
| 2001/0056298 A1 | 12/2001 | Brown et al. | |
| 2002/0107560 A1 | 8/2002 | Richter | |
| 2002/0188243 A1* | 12/2002 | Brisken et al. | 604/22 |
| 2003/0050688 A1 | 3/2003 | Fischell et al. | |
| 2003/0078649 A1 | 4/2003 | Camrud et al. | |
| 2003/0083731 A1 | 5/2003 | Kramer et al. | |
| 2003/0114912 A1 | 6/2003 | Sequin et al. | |
| 2003/0125791 A1 | 7/2003 | Sequin et al. | |
| 2003/0139796 A1 | 7/2003 | Sequin et al. | |
| 2003/0139803 A1 | 7/2003 | Sequin et al. | |
| 2003/0187497 A1 | 10/2003 | Boylan et al. | |
| 2003/0216804 A1 | 11/2003 | DeBeer et al. | |
| 2004/0002753 A1 | 1/2004 | Burgermeister et al. | |
| 2004/0006381 A1 | 1/2004 | Sequin et al. | |
| 2004/0059410 A1 | 3/2004 | Cox | |
| 2004/0073284 A1* | 4/2004 | Bates et al. | 623/1.11 |
| 2004/0093077 A1 | 5/2004 | White et al. | |
| 2004/0098080 A1 | 5/2004 | Lau et al. | |
| 2004/0098091 A1 | 5/2004 | Erbel et al. | |
| 2004/0167616 A1 | 8/2004 | Camrud et al. | |
| 2004/0176837 A1 | 9/2004 | Atladottir et al. | |
| 2004/0243133 A1 | 12/2004 | Materna | |
| 2004/0249446 A1 | 12/2004 | Patel et al. | |
| 2005/0002981 A1* | 1/2005 | Lahtinen et al. | 424/423 |
| 2005/0015136 A1 | 1/2005 | Ikeuchi et al. | |
| 2005/0033399 A1 | 2/2005 | Richter | |
| 2005/0038500 A1 | 2/2005 | Boylan et al. | |
| 2005/0075716 A1 | 4/2005 | Yan | |
| 2005/0096726 A1 | 5/2005 | Sequin et al. | |
| 2005/0125052 A1 | 6/2005 | Iwata et al. | |
| 2005/0159808 A1 | 7/2005 | Johnson et al. | |
| 2005/0182479 A1 | 8/2005 | Bonsignore et al. | |
| 2005/0192663 A1 | 9/2005 | Lau et al. | |
| 2005/0222671 A1 | 10/2005 | Schaeffer et al. | |
| 2006/0004437 A1 | 1/2006 | Jayaraman | |
| 2006/0015171 A1 | 1/2006 | Armstrong | |
| 2006/0015172 A1 | 1/2006 | Boyle et al. | |
| 2006/0015173 A1 | 1/2006 | Clifford et al. | |
| 2006/0030931 A1 | 2/2006 | Shanley | |
| 2006/0036315 A1 | 2/2006 | Yadin et al. | |
| 2006/0060266 A1 | 3/2006 | Bales et al. | |
| 2006/0064154 A1 | 3/2006 | Bales et al. | |
| 2006/0064155 A1 | 3/2006 | Bales et al. | |
| 2006/0069424 A1 | 3/2006 | Acosta et al. | |
| 2006/0074480 A1 | 4/2006 | Bales et al. | |
| 2006/0085057 A1 | 4/2006 | George et al. | |
| 2006/0095123 A1 | 5/2006 | Flanagan | |
| 2006/0111771 A1 | 5/2006 | Ton et al. | |
| 2006/0122964 A1 | 6/2006 | Stinson et al. | |
| 2006/0129222 A1 | 6/2006 | Stinson | |
| 2006/0136037 A1 | 6/2006 | DeBeer et al. | |
| 2006/0184231 A1 | 8/2006 | Rucker | |
| 2006/0259123 A1 | 11/2006 | Dorn | |
| 2007/0168019 A1 | 7/2007 | Amplatz et al. | |
| 2007/0173927 A1 | 7/2007 | Shin et al. | |
| 2008/0109029 A1* | 5/2008 | Gurm | 606/194 |
| 2008/0154356 A1 | 6/2008 | Obermiller et al. | |

FOREIGN PATENT DOCUMENTS

| | | |
|---|---|---|
| EP | 1 034 751 A2 | 9/2000 |
| EP | 1 290 987 | 3/2003 |
| EP | 1 512 381 | 3/2005 |
| EP | 1 523 959 | 4/2005 |
| EP | 1 563 806 | 8/2005 |
| GB | 2 378 137 A | 2/2003 |
| WO | WO 01/74273 A1 | 10/2001 |
| WO | WO 01/76508 A2 | 10/2001 |
| WO | WO 02/15823 | 2/2002 |
| WO | WO 03/047651 | 6/2003 |
| WO | WO 2004/017865 | 3/2004 |
| WO | WO 2004/096092 | 11/2004 |
| WO | WO 2004/110313 A1 | 12/2004 |
| WO | WO 2005/094728 | 10/2005 |
| WO | WO 2006/087621 | 8/2006 |

OTHER PUBLICATIONS

Van Der Giessen, Willem J., et al., "Mechanical Features and In Vivo Imaging of a Polymer Stent", International Journal of Cardiac Imaging, 1993, 9: 219-226.

* cited by examiner

METHOD FOR TREATING A BODY LUMEN

This nonprovisional application claims the benefit of U.S. Provisional Application No. 61/086,048, filed Aug. 4, 2008.

FIELD OF THE INVENTION

The present invention relates to a method for treating a body conduit/lumen, such as a blood vessel, in an animal such as a human. In embodiments, the treatment is directed to a conduit that has an undesired reduced diameter (e.g., an area of stenosis in a blood vessel). Examples of conduits that may be treated by the method of the present invention include, for example, blood vessels that have an undesired reduced diameter, such as may result from an obstruction within the blood vessel and/or a spasm of the blood vessel such as may occur in connection with myocardial infarction, but are not limited to such conduits.

BACKGROUND

The treatment of body lumens that have an undesired reduced diameter is often difficult because of an inability to determine the natural diameter of the lumen. For example, the healthy and normal diameter of a blood vessel may be unknown when the blood vessel has an undesired reduced diameter. For example, in a patient suffering from an acute myocardial infarction, the proper selection of a stent for treatment of the blood vessel is difficult because the diameter of the blood vessel has suddenly changed. Various factors can cause such changes, such as contractile spasms of the blood vessel and/or the presence of blood clots (thrombi).

Treating bodily conduits that have an undesired reduced diameter by means of a radially expandable tubular implant with a cutout or meshed structure, currently called a "stent," is known. This device may be introduced in an unexpanded/contracted state into the conduit to be treated and delivered to the area of the conduit that has an undesired reduced diameter. The device is then radially expanded, particularly by means of an inflatable balloon, or, when it has a self-expandable structure, the stent may be released from a sheath that contains the stent in its contracted state.

As discussed above, various stents are available to treat such conditions, including balloon-expandable stents and self-expanding stents. When using stents, those of ordinary skill in the art sometimes select an expanded stent size of 100-120% of the presumed normal size of the lumen. That is, the stent is allowed to expand within the target location to a size that is the same size as the presumed normal size of the target location, up to a size that is 20% larger than the presumed normal size of the target location. This can ensure that the stent is not under-sized, and thus that the stent is firmly anchored in place. With self-expanding stents in particular, it further ensures that there is continuous radial force anchoring the stent in place.

When balloon-expandable stents are selected in place of self-expanding stents, great care (and thus extra time in a situation such as a myocardial infarction where time is of the essence in treatment) must be taken in selecting an appropriately sized stent to avoid any danger that the stent may be under-sized when fully expanded. However, issues may remain due to the possibility of the lumen size continuing to change over time, and over-sizing of balloon-expanded stents might cause damage such as rupture of a lumen wall. In addition, with any stent that remains in the lumen, the stent itself may cause problems over time, such as causing thrombosis formation within a blood vessel. This is even more relevant with drug eluting stents, e.g., stents that elute anti-restenotic drugs, since the polymer coating on these stents may be responsible for late stent thrombosis when the stent is not well apposed to the vessel wall. Such issues could be addressed by bioresorbable stents.

There remains a demand for methods for effectively treating bodily conduits, for example, bodily conduits that have an undesired reduced diameter.

SUMMARY

In embodiments of the present invention, a target diameter of a target location of a bodily lumen to be treated is determined, and a self-expanding stent in a contracted configuration is delivered to the target location. The self-expanding stent is selected such that the self-expanding stent, in a fully expanded configuration, has a diameter that is more than 50% larger than the target diameter (e.g., the stent is selected to have an expanded diameter of more than 150% of the target diameter of the bodily lumen), for example, more than 55% larger, more than 60% larger, e.g., 60-100% or 60-150% larger than the target diameter. The stent may be allowed to initially self-expand to an expanded lumen diameter after any contractile spasms and/or blood clots are remedied in the lumen. In addition, the stent may thereafter continue to self-expand over time such that the stent slowly migrates inside and beyond the wall of the lumen where it avoids the risk of thrombosis formation.

Advantages of embodiments include that stent selection may be much easier and quicker because variations of the degree of over-sizing of the stent do not require detailed consideration, and selection of the target diameter need not be precise or determined in a time-consuming manner, as long as the minimum amount of over-sizing is present. Thus a "one-size-fits-all" approach may be used, based, e.g., on readily observable patient morphology (e.g., gender, age, weight and the like). Alternatively, more tailored approaches such as sizing based on upstream lumen diameter with angiographic images and/or parallel branch diameter are also available for situations where time permits determination of an upstream or parallel branch diameter.

Advantages of embodiments include that the lumen is expanded to its natural diameter or a slightly larger diameter. In embodiments, a short-term benefit may include the stent self-expanding to a vessel diameter while or after contractile spasms and/or blood clots or the like are remedied in the lumen. The stent may thereafter continue to slowly expand over time such that the stent slowly migrates inside, through and then outside of the lumen. In embodiments, the stent may continue to provide structural support to the lumen from the outside of the lumen even after such migration thanks to positive remodelling of the vessel. Also, after the stent migrates outside the lumen, it becomes less likely to itself become a source of problems in the lumen, such as a source of thrombus formation. Thus the need for anti-thrombotic medication, for example in the form of prolonged anti-platelet therapy, may be reduced or avoided in embodiments. The stent may be, but in embodiments need not be, bioresorbable or drug-eluting. It may be, or may not be, used in connection with angioplasty.

Methods according to the invention may be utilized for treating various bodily conduits/lumens, including bifurcations, such as vascular bifurcations.

An example of a self-expanding stent that may be utilized in embodiments is described in prior pending U.S. patent application Ser. No. 11/884,114, the entire disclosure of which is hereby incorporated by reference in its entirety, and the following discussion and drawings, but the invention is not limited to such disclosure. That disclosure focuses on embodiments that permit opening of a side wall of the stent to one or more side branches of the lumen. While that disclosure focuses to some extent on Y-shaped bifurcations in which the present invention is useful, embodiments of the present invention, as discussed above, may be used in various bodily conduits/lumens. For example, embodiments of the present invention may be used in un-branched lumens, or in lumens with one or more side branches. For acute treatments or the like, the branches may be ignored, the diameters of the branches may be underestimated, and/or the branches may be considered insignificant during initial stent placement. Accordingly, in embodiments, access to the side branch(es) may be provided during the stent placement procedure, or optionally stenting thereof may be provided in subsequent treatments that are one to twenty-four hours, one to seven days, one to four weeks, one to twelve months, or even one or more years later.

DETAILED DESCRIPTION OF EMBODIMENTS

Figure 1:
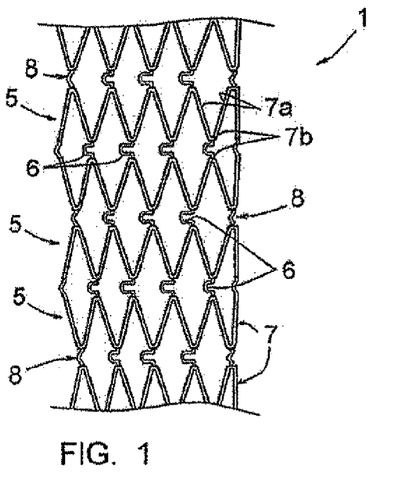
FIG. 1 is a side view of a portion of a stent; in this view, only the structures situated in the foreground are represented, for clarity of the drawing.

FIG. 1 depicts a radially expandable tubular implant 1, currently called a "stent." The stent 1 comprises a plurality of circular (annular) portions 5 in a cutout structure and bridges 6 connecting the circular portions 5 to each other. In embodiments, the bridges may optionally be breakable during deployment. Each circular portion 5 is formed by a zigzag portion (e.g., wire that may have a substantially flat, polygonal (e.g., rectangular or tetrahedral), round or other cross-sectional shape or a tube that is cut-out by laser) 7 whose extremities are connected to each other. Different segments 7a that are formed by the wire 7 preferably have substantially identical lengths.

The wire 7 is formed of a material such that the stent 1 may pass from a radially contracted state to a radially expanded state, by deformation of the bends 7b that define the different segments 7a. The radially contracted state allows engagement of the stent 1 in a sheath that is used to deliver the stent 1 to the area of a bodily conduit that has an undesired reduced diameter, and the radially expanded state allows the stent 1 to give the bodily conduit the diameter that the conduit must have (i.e., the natural diameter). The stent 1 is self-expandable, that is, the stent 1 expands from its radially contracted state to its radially expanded state when it is released by said routing sheath. The sheath may be retracted to allow the stent to self-expand. The wire 7 may, for example, be formed of a shape-memory metal such as the nickel-titanium alloy known under the name "nitinol." The wire 7 also may be formed of other materials, including, for example, various other metals (as used herein, "metals" includes elemental metals and metal-containing alloys).

In embodiments, treatment may be directed to un-branched conduits, or directed to conduits with one or more branches. In embodiments, which may include acute treatments or the like, the branches may be ignored during initial stent placement, and side access may be provided in subsequent treatments that are one to twenty-four hours, one to seven days, one to four weeks, one to twelve months or even years later, or access to the side branch(es) and optional stenting thereof may be provided during the stent placement procedure.

The self-expanding stent 1 is delivered in a contracted configuration to the target location. In a fully self-expanded configuration, the stent 1 has a diameter that is more than 50% larger than the target diameter(s) over an entire length of the stent 1. The stent 1 may be configured to exert a substantially constant radially outward force against the bodily conduit over substantially a full range of expansion of the stent 1. The target diameter may be substantially constant along the length of the target location, or may change over the length of the target location. Thus, for example in an un-branched target location, the target diameter may be relatively uniform. As another example, in a branched target location, the target diameter may change substantially at the area of branching. The fully-expanded diameter of the stent in either instance may be uniform or change over the length of the stent.

The step of determining the target diameter may be based on various factors and considerations. For example, the target diameter may be based on readily observable patient morphology (e.g., sex, age, weight and the like). In such a determination, the target diameter may have a very imprecise correlation to the natural diameter of the target location in the body conduit. The target diameter may also or alternatively, for example, be based on a feature with a more precise correlation to the natural diameter of the target location, such as a diameter of the body conduit at a location upstream of the target location, and/or on a diameter of a parallel branch(es) that is included in a branching system with the body lumen, such as a coronary tree.

In embodiments, the stent 1, in a fully self-expanded configuration, has a diameter that is more than 50% larger than the target diameter, for example, 51-150% larger than the target diameter over an entire length of the self-expanding stent 1. For example, the stent 1 in a fully expanded configuration has a diameter that is more than 55%, 60%, 65%, 70%, 75%, 80%, 100%, 110%, 120%, 130%, 140% or 150% of the target diameter over an entire length of the self-expanding stent.

The body conduit to be treated may be a blood vessel. In embodiments, the target location may be a site of an undesired reduced diameter of the flow passage through the blood vessel, such as a site of a contractile spasm of the blood vessel, a site of a thrombus located in the blood vessel, and/or a site of trauma to the blood vessel.

Figures 6, 7, 8, 9:
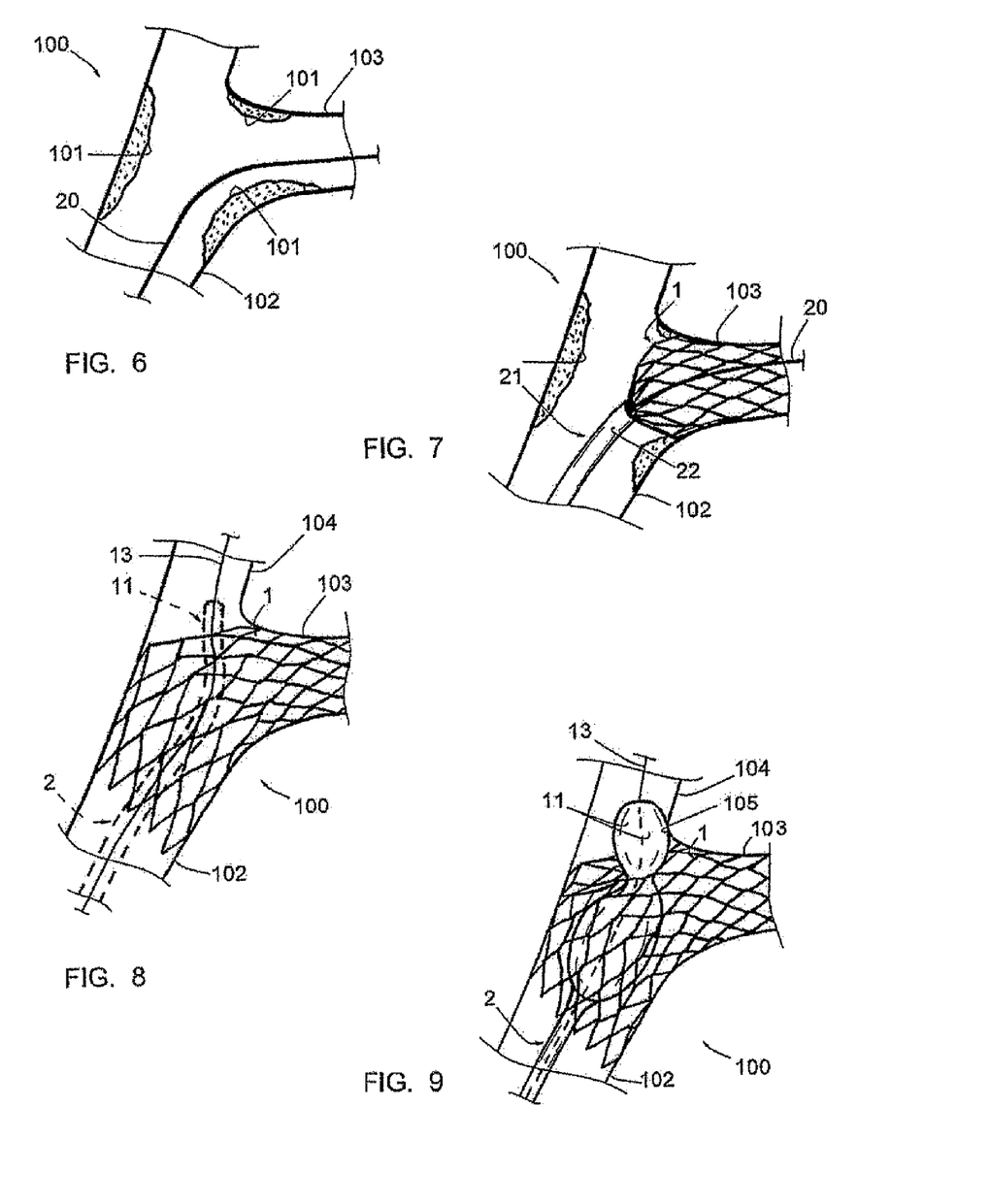
FIGS. 6 to 11 are views of different successive steps of positioning a stent at an area of a bifurcation.

In embodiments, an obstruction of the body conduit at the target location, such as a thrombus, or atheroma plaques 101, as depicted in FIG. 6, may be treated before the stent 1 is delivered to the target location. For example, the treatment of the obstruction may include supplying a thrombolytic agent or an anti-spastic agent to the target location prior to the delivery of the stent 1 to the target location.

In embodiments, the treatment of the obstruction may include mechanical treatment. For example, the treatment of the obstruction may include deoccluding the obstruction with a percutaneous de-occluding tool, debulking the obstruction with a de-bulking tool, and/or performing balloon angioplasty, at the site of the obstruction.

In addition, the obstruction may be treated prior to the delivery of the stent 1 by aspiration of a thrombus, or by laser treatment of the obstruction.

As discussed above, in embodiments, treatment may be directed to un-branched conduits, or to conduits with one or more side branches. Various self-expanding stents may be utilized in embodiments of the present invention. For example, the following description focuses on embodiments that permit opening of a side wall of the stent to one or more side branches of the lumen.

In embodiments, the stent 1 may include breakable bridges 6 that connect the adjacent bends 7b of two consecutive circular portions 5. In the embodiment depicted in FIG. 2, each of the breakable bridges 6 has a hat shape, that is, they comprise two lateral branches 6a for connecting to the respective bends 7b and a curved central part 6b. Due to this shape, the bridges 6 have a certain flexibility that, in conjunction with the flexibility that the circular portions 5 themselves have, allows the stent 1 to have a certain longitudinal flexibility itself when it is in the radial expansion state, and also allows for a bend of at least 10 degrees when placed in a bifurcation. Because of this longitudinal flexibility, as depicted in FIG. 8, a part of stent 1 may be positioned in the main conduit of a bifurcation while the other part of the stent 1 is positioned in one of secondary conduits of the bifurcation even when the main conduit and the secondary conduit form an angle with each other.

Figure 2:
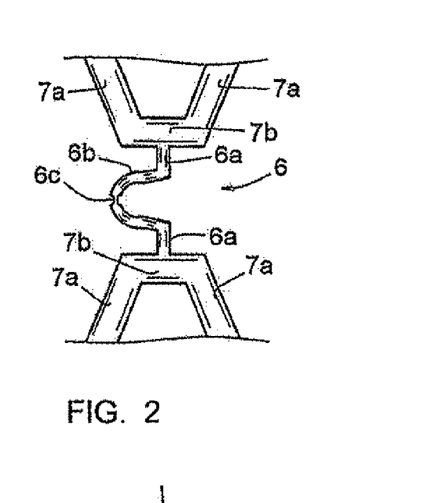
FIG. 2 is a detail view, at a very enlarged scale, of the stent of FIG. 1.

The rounded portion 6b of each bridge 6 of the stent depicted in FIG. 2 comprises a reduced median area 6c that is configured to be broken if a constraint operates to spread two adjacent circular portions 5 apart from each other. The different reduced areas 6c of the bridges 6 are situated along the same area in the longitudinal direction of the stent 1 and therefore form an area 8 of relative fragility, specific for normally resisting the constraints transmitted by the bodily conduits 102 and 103 in which the stent 1 is implanted but not resisting the separation of the two adjacent portions 5 by a separation means such as a catheter balloon 2 as described below.

Figure 3:
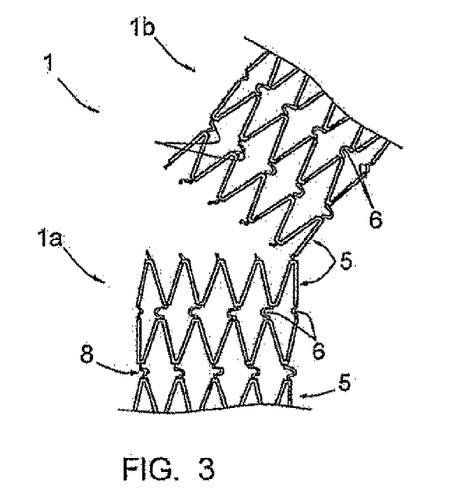
FIG. 3 is a view of a stent that is similar to the stent of FIG. 1, after the lateral opening of the stent by separation of separable bridges that comprise this stent.

As depicted in FIG. 3, the breaking of the bridges 6 at an area 8 allows the stent 1 to be largely or completely open over a significant portion of the area 8 in such a way as to form two tubular parts 1a and 1b that are partially separated.

Figure 4:
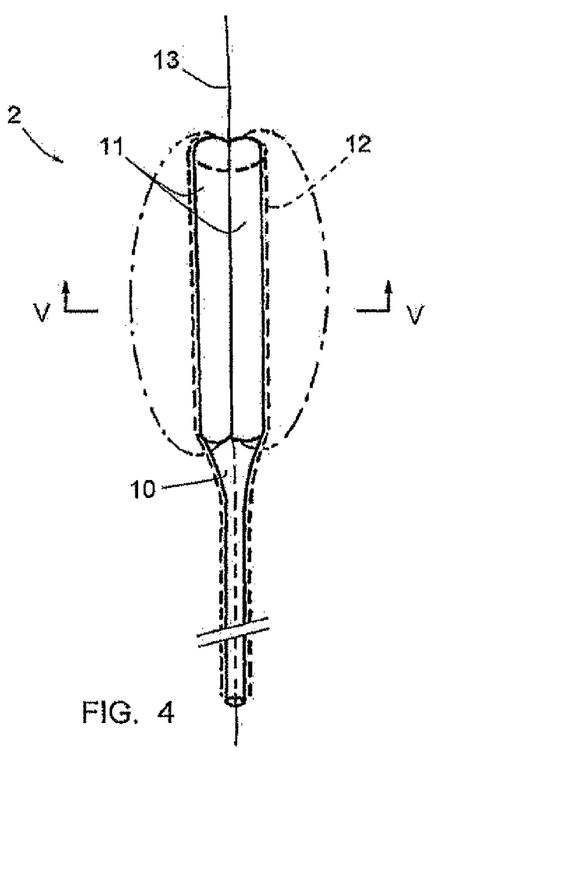
FIG. 4 is a view of a balloon catheter that may be utilized to open the stent of FIG. 3.

FIG. 4 represents a balloon catheter 2 allowing the separation of portions of the depicted stent 1 at the area of a bifurcation, that is, at an area of the separation of a principal bodily conduit into two secondary conduits. The stent 1 and the catheter 2 form a device allowing treatment of a bifurcation.

With further reference to FIG. 4, the catheter 2 may, for example, comprise an elongated body 10, two side-by-side balloons 11 forming the separation means, and an external sliding sheath 12.

The elongated body 10 presents an axial conduit extending between the balloons 11, that allows the catheter 2 to slide along an axial guiding wire 13.

Figure 5:
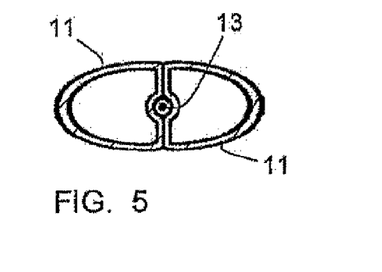
FIG. 5 is a view of the balloons of the balloon catheter of FIG. 4 in transversal section, after inflation.

The two balloons 11 are connected to a source of inflation fluid (not shown). In the deflated state, the balloons 11 are maintained by the sheath 12 in a radial contraction position, represented as solid lines in FIG. 4, and may be inflated until they take the form represented as interrupted lines in FIG. 4 and as depicted in the cross-sectional view of FIG. 5. As depicted in FIG. 5, each balloon 11 has a section substantially in the shape of a "D" and is bracketed to the other balloon by its plane wall, in such a way that the two balloons 11 conjointly form a balloon having a substantially annular shape in a transversal section.

In practice, in the treatment of a bifurcation 100 that has atheroma plaques 101 along the inner walls of the conduits of the bifurcation, a guiding wire 20 is first introduced percutaneously through the main conduit 102 and the secondary conduit 103 to be treated (see FIG. 6).

A catheter 21 is then advanced over the wire 20 into the main conduit 102 and then into the secondary conduit 103. The catheter 21 contains the stent 1 that is maintained in a state of radial contraction such as by an exterior sliding sheath 22. When the distal extremity of the catheter 21 is inside the secondary conduit 103, the sheath 22 may be slid in such a way so as to release the stent 1, which is deployed in the secondary conduit 103 then in the main conduit 102, as depicted in FIGS. 7 and 8. The sliding of the sheath 22 may be a retraction of sheath 22 away from the distal extremity of the catheter 21. The deployment of the stent 1, allows the atheroma plaques 101 to be compressed such that the conduits 102 and 103 regain adequate diameters (e.g., substantially natural diameters). The stent has a significantly larger diameter than the target diameter over the whole length of the stent. Thus a stent with a substantially uniform diameter will have a diameter more than 50% larger than the size of the main conduit 102 and substantially more than such oversizing for the secondary conduit 103.

Either during the deployment procedure or later as discussed above, the guiding wire 13 is advanced into the main conduit 102 and through an opening in the wall of stent 1, and in the other secondary conduit 104 of the bifurcation 100, as depicted in FIG. 8. The guiding wire 13, named a guidewire, is advantageously passed through an opening located closest to the "carena" 105, that is, the area of bifurcation 100 corresponding to the departure of the two secondary conduits 103 and 104. The zigzag wire structure of portions 5, depicted in FIG. 8, defines only the open meshes of the side of areas 8, in such a way that the practitioner is ensured of engaging the guidewire 13 between two portions 5 at area 8. The catheter 2 is then advanced over the guidewire 13, and the balloons 11 are advanced through the stent 1, as depicted in interrupted lines in this FIG. 8.

Figure 10:
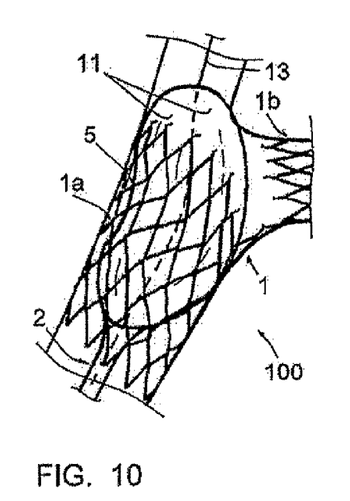

The balloons 11 are then inflated and exert a force on the two circular portions 5 between which they are engaged, such that the two portions 5 separate from each other. The inflation of the balloons causes the rupture of the reduced areas 6c of the bridges 6 situated between the two circular portions 5, with the optional exception of one or more bridges 6 situated diametrically opposed to a bridge at the area of which the balloons 11 crossed stent 1 (see FIGS. 9 and 10), in such a way that the two tubular parts 1a and 1b are thus formed.

Figure 11:
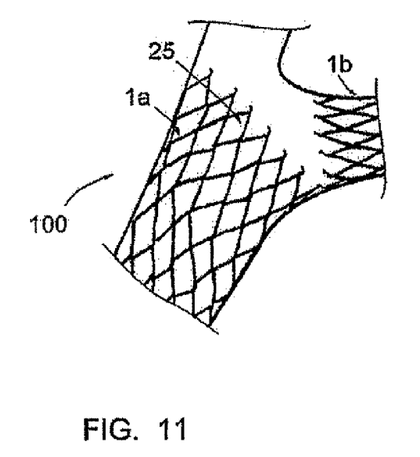

The balloons 11 are then deflated, and then the catheter 2 and the guiding wire 13, are withdrawn from the patient's vasculature (see FIG. 11).

Figure 12:
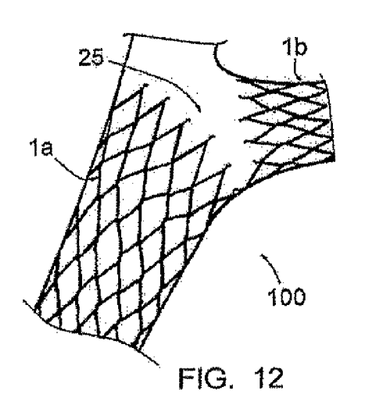
FIGS. 12 and 13 are views of a stent after positioning, according to two other possible positionings of this stent in a bifurcation.
Figure 13:
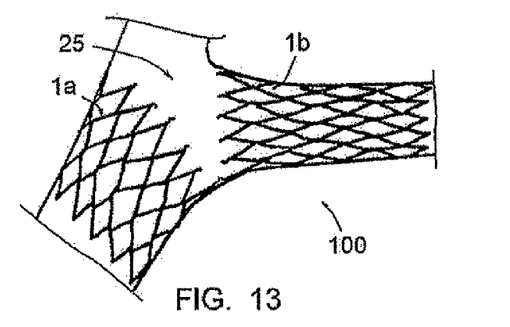

FIGS. 12 and 13 depict that a certain leeway in the positioning of the stent 1 in the bifurcation 100 is made possible by the existence of the plurality of areas 8 comprised of the series of bridges 6. It is therefore particularly possible to treat bifurcations 100 having different positionings of atheroma plaques 101.

Figure 14:
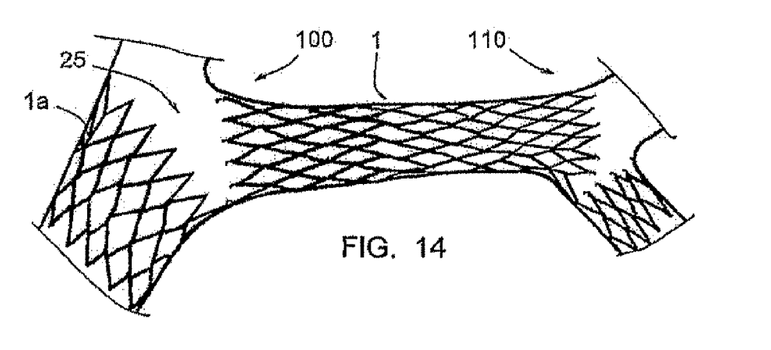
FIG. 14 is a view of a longer stent after positioning in an area of two bifurcations.

FIG. 14 depicts that the stent 1 may have a long length and that it may be the subject of two or more lateral openings such as the aforementioned, one at the area of a bifurcation 100 as described above, the other(s) at the area(s) of another bifurcation(s) 110, or that two stents 1 may be positioned successively and opened laterally.

Figure 15:
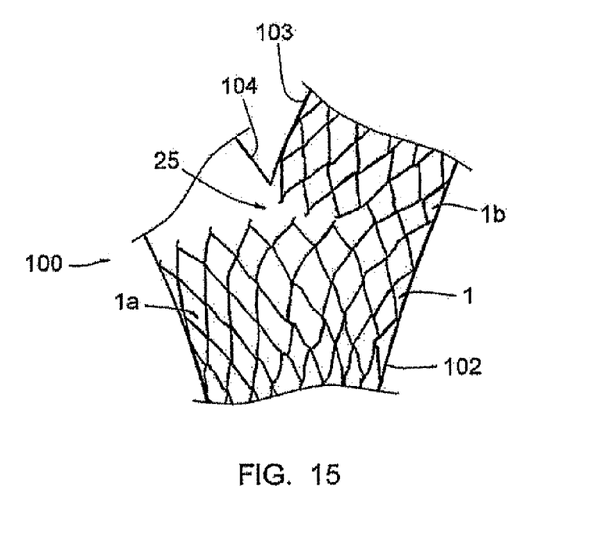
FIG. 15 is a view of a stent after being positioned in a bifurcation in a transition area between the main conduit and the secondary conduits, the stent portion in the main conduit having a truncated conical form.
Figure 16:
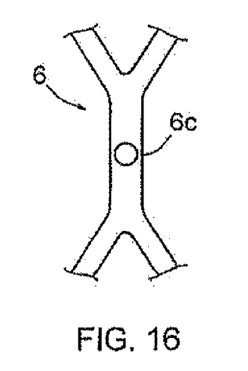
FIGS. 16 to 21 have similar views to FIG. 2 of different variations of embodiment of said separable bridges.
Figure 17:
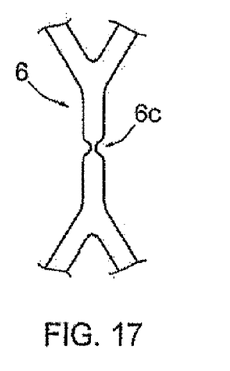
Figure 18:
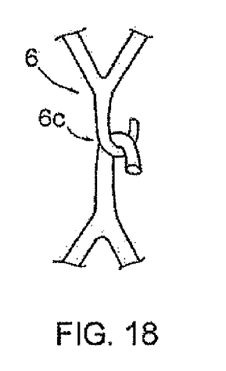

FIG. 15 depicts the case of a bifurcation presenting an area of transition that is flared between the main conduit 102 and the secondary conduits 103 and 104. Part 1a of the stent 1 may self-expand in such a way so as to be adapted to the flared form of the transition area. The stent self-expands such that the stent 1 has a diameter that is more than 50% larger than the diameter of a target diameter over an entire length of the self-expanding stent 1.

Figure 19:
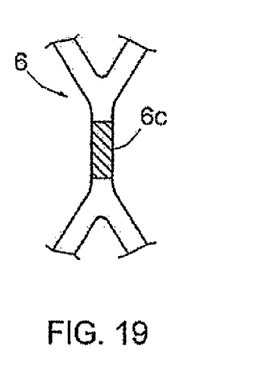
Figure 20:
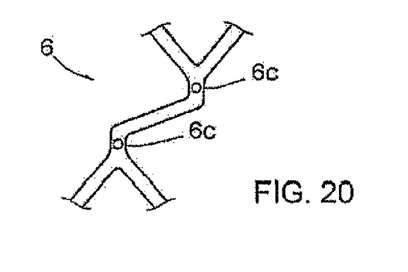
Figure 21:
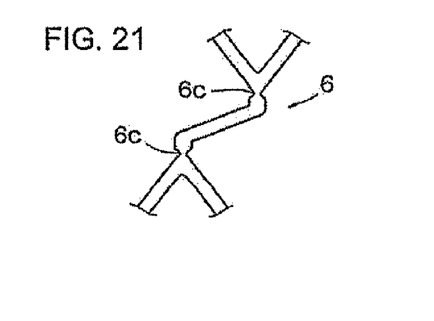

FIGS. 16 to 21 depict that each bridge 6 may be parallel to the longitudinal axis of the stent (FIGS. 16 to 19) or oblique with relation to this longitudinal axis (FIGS. 20 and 21).

Each bridge 6 may comprise one or more areas 6c that may be of reduced resistance, for example, in the form of one or more thinnings of the section of the bridge, cuts, circular perforations provided in the bridge (FIGS. 16, 17, 20, 21), or of a grooved or striated area.

Each bridge 6 may also or alternatively, for example, comprise one or more areas 6c in a material different from the material constituting the rest of the bridge, optionally suitable for being broken under the separation action exerted by the balloon 11 (FIG. 19). Each bridge 6 may comprise two parts 6b forming interconnected hooks (FIG. 18), specific for being deformed to be separated under the action of separation means, or forming a microlevers-type system (called "MEMS"), specific for being opened with the help of a cryotherapy balloon to cool the microlevers.

As appearing from the aforesaid, embodiments of the invention provide devices and methods for allowing the treatment of bodily conduits, including bodily conduits at a bifurcation, that have the decided advantage of being able to be positioned according to an operation that is shorter and less delicate to carry out than a device and methods known in the art.

Figures 22, 23, 24, 25, 26, 27:
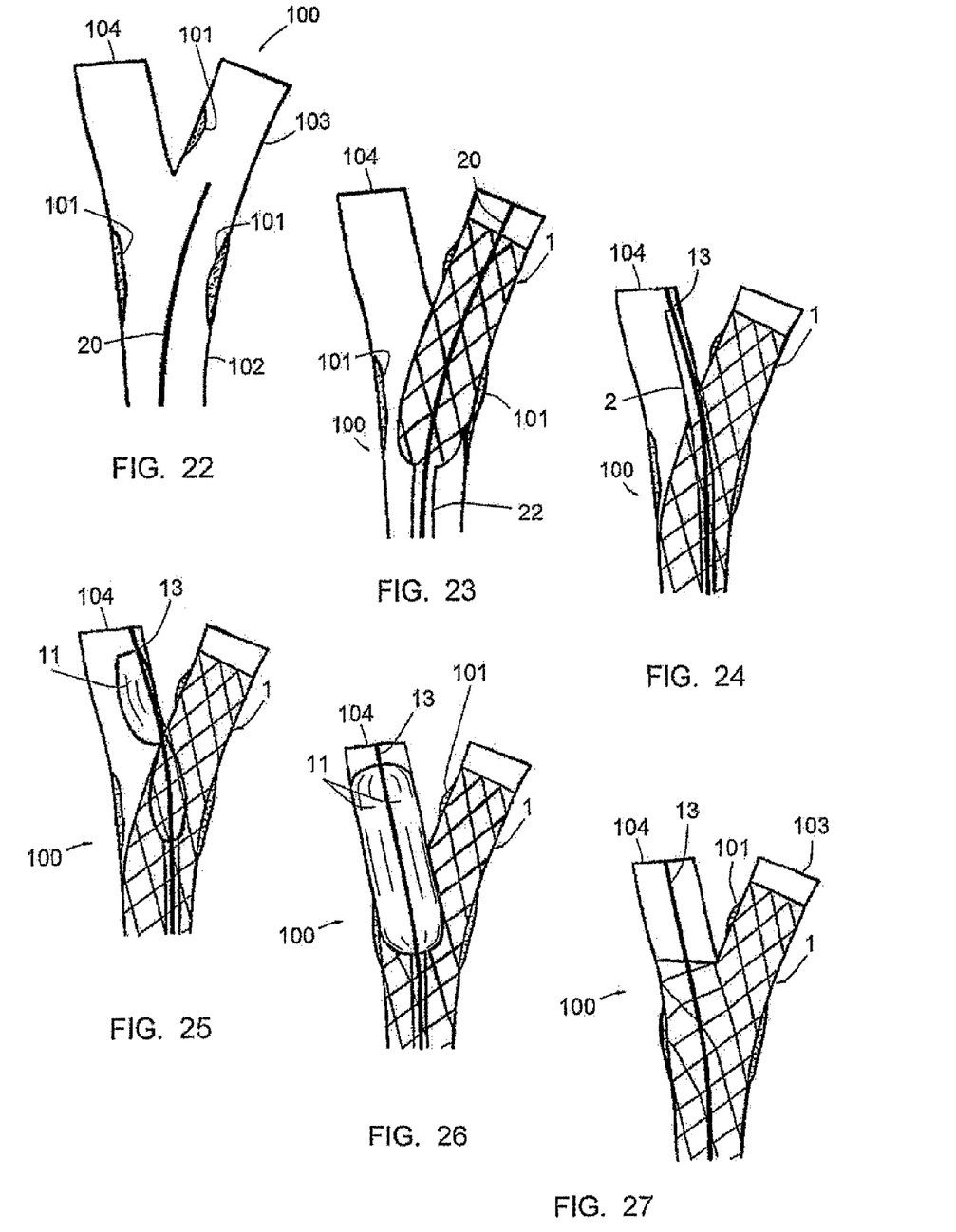
FIGS. 22 to 27 are views of different successive steps of positioning a stent at the area of a Y-shaped bifurcation.

FIGS. 22 to 27 depict different successive steps of positioning a stent at the area of a Y-shaped bifurcation. These figures respectively depict the same steps as do FIGS. 6 to 11. After separation by the balloon on FIG. 26, the stent 1 continues to expand to conform to the shape of the main conduit (FIG. 27). Particularly over time, the stent 1 may expand to a diameter that is more than 50% larger than the target diameter of the main conduit. For example, the stent 1 may expand to a diameter that is more than 55% larger, more than 60% larger, more than 70% larger, or more than 150% large, than the main conduit target diameter over an entire length of the stent 1. In doing so, the stent may migrate through the walls of the conduit, optionally providing external support of the conduit. The stent clearly supports the frustoconical shape of the main conduit, which includes part of the side branch ostium.

It goes without saying that the invention is not limited to the embodiments described above by way of example but that it extends to all embodiments of the invention. For example, portions 5 of stent 1 may have a meshed structure; means provided to ensure engagement of a balloon through a selected area 8 may comprise marking means for each area 8, for example in the form of radio-opaque markers; the balloon 11 may be formed from two balloons as described previously or from a single balloon; separation means could be one or more balloons, including cryotherapy balloons, a small expansion tool, like small forceps or pliers, at the distal end of a catheter and actuated from the proximal end with wires extending in the lumen of the said catheter, or other separation means; the stent can be a drug eluting stent.

Figure 28:
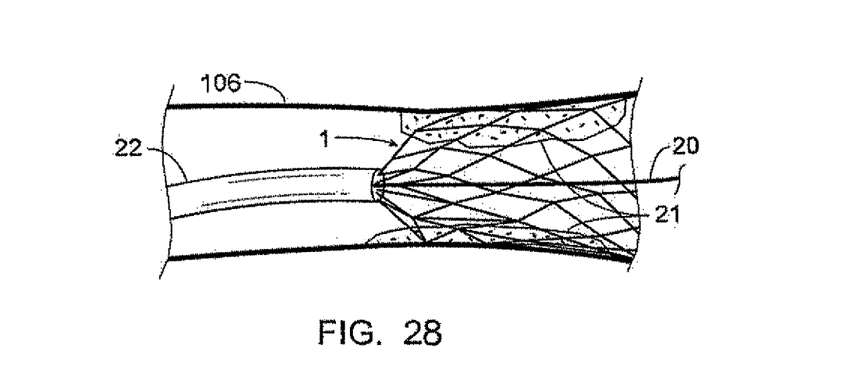
FIGS. 28-30 are views of different successive steps of positioning a stent in an un-branched conduit.
Figure 29:
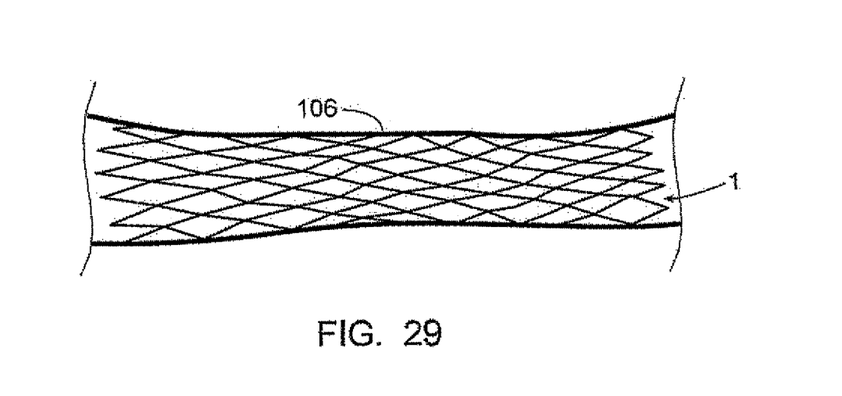
Figure 30:
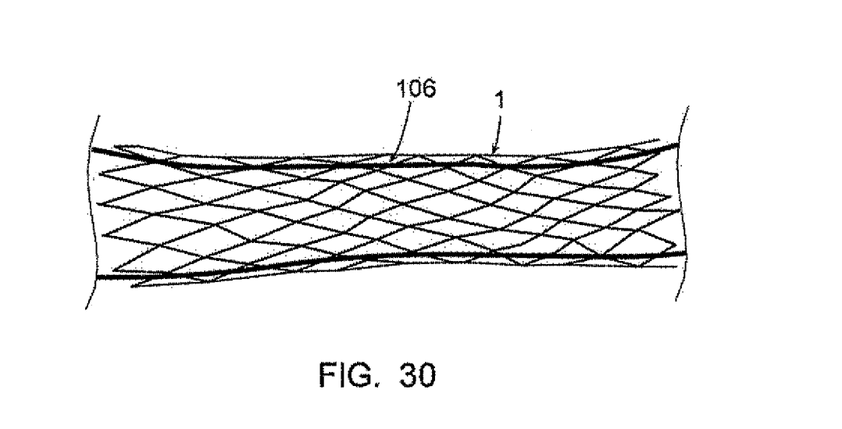

While the above disclosure focuses to some extent on Y-shaped bifurcations in which the present invention is useful, embodiments of the present invention may also be used in un-branched lumens, or lumens with one or more side branches. For example, FIG. 28 depicts the deployment of the stent 1 in an un-branched conduit 106. FIG. 29 depicts the un-branched conduit 106 in an expanded state, in which the un-branched conduit 106 has substantially regained its natural diameter, as a result of the self-expansion of the stent 1. FIG. 30 depicts the stent 1 after the gradual migration of the stent 1 through the walls of the un-branched conduit 106.

The invention claimed is:

1. A method for the treatment of a body lumen, comprising:
   determining a target diameter of said lumen in a target location in said lumen, said target diameter closely approximating a natural diameter of the lumen at the target location, the natural diameter being a diameter of the lumen unobstructed by plaque or other occlusions at the target location;
   delivering a self-expanding metal stent in a contracted configuration to said target location, wherein said self-expanding metal stent, in a fully self-expanded configuration, has a diameter that is more than 55% larger than said target diameter over an entire length of said self-expanding metal stent; and
   allowing the self-expanding metal stent to self-expand at said target location.

2. The method of claim 1, wherein said self-expanding stent is configured to exert a substantially constant radially outward force over substantially a full range of expansion of said stent.

3. The method of claim 1, comprising determining said target diameter based on a diameter of said body lumen at a location upstream of said target location.

4. The method of claim 1, wherein said lumen is part of a branching system of lumens, comprising determining said target diameter based on a diameter of at least one parallel branch of said branching system of lumens.

5. The method of claim 4, wherein said branching system is a coronary tree.

6. The method of claim 1, comprising treating an obstruction of said lumen at said target location before delivering said self-expanding stent to said target location.

7. The method of claim 6, wherein treating said obstruction comprises supplying a thrombolytic agent to said target location prior to delivering said self-expanding stent to said target location.

8. The method of claim 6, wherein treating said obstruction comprises supplying an anti-spastic agent to said target location prior to delivering said self-expanding stent to said target location.

9. The method of claim 6, wherein treating said obstruction comprises mechanical treatment of said obstruction.

10. The method of claim 9, wherein said mechanical treatment comprises deoccluding said obstruction with a percutaneous de-occluding tool.

11. The method of claim 9, wherein said mechanical treatment comprises debulking said obstruction with a percutaneous de-bulking tool.

12. The method of claim 9, wherein said mechanical treatment comprises performing balloon angioplasty at said obstruction.

13. The method of claim 6, wherein treating said obstruction comprises aspiration of a thrombus.

14. The method of claim 6, wherein treating said obstruction comprises laser treatment of said obstruction.

15. The method of claim 1, wherein said self-expanding stent, in a fully self-expanded configuration, has a diameter that is more than 60% larger than said target diameter over an entire length of said self-expanding stent.

16. The method of claim 1, wherein said self-expanding stent, in a fully self-expanded configuration, has a diameter that is more than 65% larger than said target diameter over an entire length of said self-expanding stent.

17. The method of claim 1, wherein said self-expanding stent, in a fully self-expanded configuration, has a diameter that is more than 70% larger than said target diameter over an entire length of said self-expanding stent.

18. The method of claim 1, wherein said self-expanding stent, in a fully self-expanded configuration, has a diameter that is more than 75% larger than said target diameter over an entire length of said self-expanding stent.

19. The method of claim 1, wherein said self-expanding stent, in a fully self-expanded configuration, has a diameter that is more than 80% larger than said target diameter over an entire length of said self-expanding stent.

20. The method of claim 1, wherein said self-expanding stent, in a fully self-expanded configuration, has a diameter that is up to 150% larger than said target diameter over an entire length of said self-expanding stent.

21. The method of claim 1, wherein said body lumen is a blood vessel.

22. The method of claim 21, wherein said target location is a site of an undesired reduced diameter of said blood vessel.

23. The method of claim 21, wherein said target location is a site of a contractile spasm of said blood vessel.

24. The method of claim 21, wherein said target location is a site of a thrombus located in said blood vessel.

25. The method of claim 21, wherein said target location is a site of trauma to said blood vessel.

26. The method of claim 1, wherein said target diameter is substantially constant along a length of said target location.

27. The method of claim 1, wherein said target location includes at least one side branch of said lumen.

28. The method of claim 27, comprising creating an access site through a wall of said self-expanding stent to said at least one side branch during the same procedure in which said self-expanding stent is delivered to said target location.

29. The method of claim 27, comprising creating an access site through a wall of said self-expanding stent to said at least one side branch at least 24 hours after delivering said self-expanding stent to said target location.

* * * * *